(12) United States Patent
Ingimundarson et al.

(10) Patent No.: US 8,926,537 B2
(45) Date of Patent: Jan. 6, 2015

(54) ORTHOPEDIC DEVICE FOR TREATMENT OF THE BACK

(75) Inventors: Arni Thor Ingimundarson, Gardabaer (IS); Brice Robertson, Sunnyvale, CA (US)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 13/616,130

(22) Filed: Sep. 14, 2012

(65) Prior Publication Data

US 2013/0006158 A1  Jan. 3, 2013

Related U.S. Application Data

(63) Continuation of application No. 13/249,933, filed on Sep. 30, 2011, now Pat. No. 8,303,528, which is a continuation of application No. 12/713,268, filed on Feb. 26, 2010, now Pat. No. 8,172,779.

(60) Provisional application No. 61/155,843, filed on Feb. 26, 2009, provisional application No. 61/236,649, filed on Aug. 25, 2009.

(51) Int. Cl.
*A61F 5/00* (2006.01)

(52) U.S. Cl.
USPC ............................................. 602/19

(58) Field of Classification Search
USPC ......... 602/12, 16, 19, 32, 60; 2/310–312, 338
See application file for complete search history.

(56) References Cited

U.S. PATENT DOCUMENTS

| | | | |
|---|---|---|---|
| 7,916 A | 1/1851 | Knapp | |
| 232,420 A | 9/1880 | Smith | |
| 321,145 A | 6/1885 | Spencer | |
| 321,146 A | 6/1885 | Spencer | |
| 368,699 A | 8/1887 | Zervas | |
| 386,642 A | 7/1888 | Mann | |

(Continued)

FOREIGN PATENT DOCUMENTS

| | | |
|---|---|---|
| AU | 2010271020 A1 | 2/2012 |
| AU | 2010271020 A2 | 2/2012 |

(Continued)

OTHER PUBLICATIONS

International Search Report and Written Opinion issued in PCT/2012/024619, May 16, 2012.

(Continued)

*Primary Examiner* — Michael A. Brown
(74) *Attorney, Agent, or Firm* — Workman Nydegger

(57) ABSTRACT

In an embodiment, an orthopedic device in the form of a lumbar support includes first and second elongate belt members, an anatomically shaped plate, and a closure system connecting the belt members to the plate. The closure system is arranged to move the belt members relative to the plate, and connects to the belt members via a flexible belt attachment which removably secures to the belt members. The closure system includes tensioning elements corresponding to the belt members, and a pulley system connecting to the tensioning elements. The closure system is slidably mounted to the plate and arranged to the belt members relative to the plate between opposed linear directions. The plate has various contours which provide pressure distribution over a lumbar region of a back. Anatomically shaped and resiliently formed handles secure to the tensioning elements and the belt members.

16 Claims, 10 Drawing Sheets

(56) References Cited

U.S. PATENT DOCUMENTS

| | | |
|---|---|---|
| 507,172 A | 10/1893 | Shelden |
| 571,749 A | 11/1896 | Colton |
| 596,849 A | 1/1898 | Combier |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 772,926 A | 10/1904 | Colton |
| 787,894 A | 4/1905 | Colton |
| 888,490 A | 5/1908 | Haas |
| 1,124,596 A | 1/1915 | Dalpe |
| 1,316,915 A | 9/1919 | Meyer et al. |
| 1,393,188 A | 10/1921 | Whiteman |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,219,475 A | 10/1940 | Flaherty |
| 2,543,370 A | 11/1948 | Hittenberger |
| 2,554,337 A | 5/1951 | Lampert |
| 2,630,801 A | 3/1953 | Mest et al. |
| 2,696,011 A | 12/1954 | Galdik |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,128,514 A | 4/1964 | Parker et al. |
| 3,274,996 A | 9/1966 | Jewett |
| 3,351,053 A | 11/1967 | Stuttle |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A * | 5/1971 | Schultz ............... 602/19 |
| 3,771,513 A | 11/1973 | Velazquez |
| 3,812,850 A | 5/1974 | Reiman |
| 3,902,503 A | 9/1975 | Gaylord, Jr. |
| 3,920,008 A | 11/1975 | Lehman |
| 3,927,665 A | 12/1975 | Wax |
| 3,945,376 A | 3/1976 | Kuehnegger |
| 4,055,168 A | 10/1977 | Miller et al. |
| 4,114,788 A | 9/1978 | Zufich |
| 4,173,973 A | 11/1979 | Hendricks |
| 4,230,101 A | 10/1980 | Gold |
| 4,285,336 A | 8/1981 | Oebser et al. |
| 4,383,523 A | 5/1983 | Schurman |
| 4,392,489 A | 7/1983 | Wagner, Sr. |
| RE31,564 E | 4/1984 | Hendricks |
| 4,494,536 A | 1/1985 | Latenser |
| 4,502,471 A | 3/1985 | Owens |
| 4,508,110 A | 4/1985 | Modglin |
| 4,559,933 A | 12/1985 | Batard et al. |
| 4,569,336 A | 2/1986 | Wheeler |
| 4,608,971 A | 9/1986 | Borschneck |
| 4,628,913 A | 12/1986 | Lerman |
| 4,640,269 A | 2/1987 | Goins |
| 4,648,390 A | 3/1987 | Friddle |
| 4,649,574 A | 3/1987 | Michels |
| 4,677,699 A | 7/1987 | Barabe |
| 4,677,969 A | 7/1987 | Calabrese |
| 4,691,696 A * | 9/1987 | Farfan de los Godos ....... 602/19 |
| 4,697,592 A | 10/1987 | Maddux et al. |
| 4,796,610 A | 1/1989 | Cromartie |
| 4,805,605 A | 2/1989 | Glassman |
| 4,807,605 A | 2/1989 | Mattingly |
| 4,843,688 A | 7/1989 | Ikeda |
| 4,905,678 A | 3/1990 | Cumins et al. |
| 4,976,257 A | 12/1990 | Akin et al. |
| 5,105,828 A | 4/1992 | Grant |
| 5,111,807 A | 5/1992 | Spahn et al. |
| 5,120,288 A | 6/1992 | Sinaki |
| 5,121,741 A | 6/1992 | Bremer et al. |
| 5,135,470 A | 8/1992 | Reeves |
| 5,135,471 A | 8/1992 | Houswerth |
| 5,170,505 A | 12/1992 | Rohrer |
| 5,171,296 A | 12/1992 | Herman |
| 5,176,131 A | 1/1993 | Votel et al. |
| D334,063 S | 3/1993 | DeWall |
| 5,199,940 A | 4/1993 | Morris et al. |
| 5,203,765 A | 4/1993 | Friddle, Jr. |
| 5,215,518 A | 6/1993 | Rosen |
| 5,230,698 A | 7/1993 | Garth |
| 5,259,833 A | 11/1993 | Barnett |
| 5,295,947 A | 3/1994 | Muncy |
| 5,313,952 A * | 5/1994 | Hoch ............... 600/390 |
| 5,318,575 A | 6/1994 | Chesterfield et al. |
| 5,334,135 A | 8/1994 | Grim et al. |
| 5,342,289 A | 8/1994 | Munny |
| 5,363,863 A | 11/1994 | Lelli et al. |
| 5,368,552 A | 11/1994 | Williamson et al. |
| 5,383,893 A | 1/1995 | Daneshvar |
| 5,399,151 A | 3/1995 | Smith |
| 5,421,809 A | 6/1995 | Rise |
| 5,423,852 A | 6/1995 | Daneshvar |
| 5,429,587 A | 7/1995 | Gates |
| 5,435,015 A | 7/1995 | Ellis-Brewer |
| 5,437,614 A | 8/1995 | Grim |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | DeRoche |
| 5,499,965 A | 3/1996 | Sanchez |
| 5,500,959 A | 3/1996 | Yewer, Jr. |
| 5,503,314 A | 4/1996 | Fiscus |
| 5,503,620 A | 4/1996 | Danzger |
| 5,520,619 A | 5/1996 | Martin |
| 5,522,792 A | 6/1996 | Bassett et al. |
| 5,531,669 A | 7/1996 | Varnau |
| 5,548,843 A | 8/1996 | Chase et al. |
| 5,551,950 A | 9/1996 | Oppen |
| 5,558,628 A | 9/1996 | Bzoch |
| 5,569,171 A | 10/1996 | Muncy |
| 5,599,287 A | 2/1997 | Beczak, Sr. et al. |
| 5,620,412 A | 4/1997 | Modglin |
| 5,622,529 A | 4/1997 | Calabrese |
| 5,632,724 A | 5/1997 | Lerman et al. |
| 5,674,187 A | 10/1997 | Zepf |
| 5,681,270 A | 10/1997 | Klearman et al. |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,695,452 A | 12/1997 | Grim et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,724,993 A | 3/1998 | Dunfee |
| 5,725,139 A | 3/1998 | Smith |
| 5,728,054 A | 3/1998 | Martin |
| 5,746,218 A | 5/1998 | Edge |
| 5,752,640 A | 5/1998 | Prouix |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,853,378 A | 12/1998 | Modglin |

(56) References Cited

U.S. PATENT DOCUMENTS

| | | |
|---|---|---|
| 5,853,379 A | 12/1998 | Ostojic |
| 5,868,292 A | 2/1999 | Stephens et al. |
| 5,890,640 A | 4/1999 | Thompson |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,993,403 A | 11/1999 | Martin |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,117,096 A | 9/2000 | Hassard |
| RE36,905 E | 10/2000 | Noble et al. |
| 6,125,792 A | 10/2000 | Gee |
| 6,129,691 A | 10/2000 | Ruppert |
| 6,156,001 A | 12/2000 | Frangi et al. |
| 6,182,288 B1 | 2/2001 | Kibbee |
| 6,190,343 B1 | 2/2001 | Heinz et al. |
| D438,624 S | 3/2001 | Reina |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,289,558 B1 | 9/2001 | Hammerslag |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,517,502 B2 | 2/2003 | Heyman et al. |
| 6,540,703 B1 | 4/2003 | Lerman |
| 6,589,195 B1 | 7/2003 | Schwenn et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 * | 9/2003 | Smith et al. ............ 600/15 |
| 6,652,596 B2 | 11/2003 | Smith et al. |
| 6,676,617 B1 | 1/2004 | Miller |
| 6,676,620 B2 | 1/2004 | Schwenn et al. |
| 6,688,943 B2 | 2/2004 | Nagaoka |
| 6,702,770 B2 | 3/2004 | Bremer et al. |
| 6,726,643 B1 | 4/2004 | Martin |
| 6,790,191 B1 | 9/2004 | Hendricks |
| 6,802,442 B1 | 10/2004 | Thompson |
| D499,806 S | 12/2004 | Machin et al. |
| D501,078 S | 1/2005 | Cabana |
| 6,893,098 B2 | 5/2005 | Kohani |
| 6,913,585 B2 | 7/2005 | Salmon et al. |
| 6,921,375 B2 | 7/2005 | Kihara |
| 6,923,780 B2 | 8/2005 | Price et al. |
| 6,926,685 B1 | 8/2005 | Modglin |
| 6,936,021 B2 | 8/2005 | Smith |
| 6,942,630 B2 | 9/2005 | Behan |
| 6,951,547 B1 * | 10/2005 | Park et al. ............ 602/19 |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,048,707 B2 | 5/2006 | Schwenn et al. |
| 7,083,584 B2 * | 8/2006 | Coligado ............ 602/19 |
| 7,083,585 B2 * | 8/2006 | Latham ............ 602/19 |
| 7,087,032 B1 | 8/2006 | Ikeda |
| 7,101,348 B2 | 9/2006 | Garth et al. |
| 7,118,543 B2 | 10/2006 | Telles et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,201,727 B2 | 4/2007 | Schwenn et al. |
| 7,306,571 B2 | 12/2007 | Schwenn et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,473,235 B2 | 1/2009 | Schwenn et al. |
| 7,476,185 B2 | 1/2009 | Drennan |
| 7,549,970 B2 | 6/2009 | Tweardy |
| 7,578,798 B2 | 8/2009 | Rhee |
| 7,597,672 B2 | 10/2009 | Kruijsen et al. |
| 7,600,660 B2 | 10/2009 | Kasper et al. |
| 7,654,972 B2 | 2/2010 | Alleyne |
| 7,727,174 B2 | 6/2010 | Chang et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,862,529 B2 | 1/2011 | Brown |
| 7,871,388 B2 | 1/2011 | Brown |
| 7,914,473 B2 | 3/2011 | Josey |
| D636,494 S | 4/2011 | Garth et al. |
| 8,006,877 B2 | 8/2011 | Lowry et al. |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,142,377 B2 | 3/2012 | Garth et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,372,023 B2 | 2/2013 | Garth et al. |
| 8,556,840 B2 | 10/2013 | Burke et al. |
| 8,597,222 B2 | 12/2013 | Lucero et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0158097 A1 | 10/2002 | Beale |
| 2003/0000986 A1 | 1/2003 | Smith |
| 2003/0125705 A1 | 7/2003 | Ruman et al. |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2006/0011690 A1 | 1/2006 | Bareno |

(56) References Cited

U.S. PATENT DOCUMENTS

| | | | |
|---|---|---|---|
| 2006/0052733 A1 | 3/2006 | Schwenn et al. | |
| 2006/0064048 A1 | 3/2006 | Stano | |
| 2006/0079821 A1 | 4/2006 | Rauch | |
| 2006/0155229 A1 | 7/2006 | Ceriani et al. | |
| 2007/0152007 A1 | 7/2007 | Kauss et al. | |
| 2007/0179417 A1* | 8/2007 | Schwenn et al. | 602/19 |
| 2007/0185425 A1 | 8/2007 | Einarsson et al. | |
| 2008/0195010 A1 | 8/2008 | Lai et al. | |
| 2008/0208091 A1 | 8/2008 | Vollbrecht et al. | |
| 2008/0249448 A1 | 10/2008 | Stevenson et al. | |
| 2008/0262401 A1 | 10/2008 | Wagner et al. | |
| 2008/0302839 A1 | 12/2008 | Murdoch et al. | |
| 2009/0025115 A1 | 1/2009 | Duffy et al. | |
| 2009/0030359 A1 | 1/2009 | Wikenheiser et al. | |
| 2009/0062704 A1 | 3/2009 | Brown et al. | |
| 2009/0082707 A1 | 3/2009 | Rumsey | |
| 2009/0100649 A1 | 4/2009 | Bar et al. | |
| 2009/0127308 A1 | 5/2009 | Mori et al. | |
| 2009/0182253 A1 | 7/2009 | Grim et al. | |
| 2009/0192425 A1 | 7/2009 | Garth et al. | |
| 2009/0198166 A1 | 8/2009 | Slomovitz | |
| 2009/0275871 A1 | 11/2009 | Liu | |
| 2009/0287128 A1 | 11/2009 | Ingimundarson et al. | |
| 2010/0010568 A1 | 1/2010 | Brown | |
| 2010/0037369 A1 | 2/2010 | Reichert | |
| 2010/0204630 A1 | 8/2010 | Sandifer et al. | |
| 2010/0217167 A1 | 8/2010 | Ingimundarson et al. | |
| 2010/0256717 A1 | 10/2010 | Brown | |
| 2010/0268141 A1 | 10/2010 | Bannister | |
| 2010/0318010 A1 | 12/2010 | Sandifer et al. | |
| 2011/0000005 A1 | 1/2011 | Brown | |
| 2011/0009793 A1 | 1/2011 | Lucero et al. | |
| 2011/0105971 A1 | 5/2011 | Ingimundarson et al. | |
| 2011/0137221 A1 | 6/2011 | Brown | |
| 2011/0152737 A1 | 6/2011 | Burke et al. | |
| 2012/0022420 A1 | 1/2012 | Sandifer et al. | |
| 2012/0197167 A1 | 8/2012 | Kruijsen et al. | |
| 2012/0232450 A1 | 9/2012 | Garth et al. | |
| 2012/0323154 A1 | 12/2012 | Ingimundarson et al. | |
| 2013/0007946 A1 | 1/2013 | Brown | |
| 2013/0012853 A1 | 1/2013 | Brown | |
| 2013/0158457 A1 | 6/2013 | Garth et al. | |
| 2013/0190670 A1 | 7/2013 | Von Zieglauer | |
| 2013/0211302 A1 | 8/2013 | Brown | |
| 2013/0237891 A1 | 9/2013 | Fryman et al. | |
| 2013/0281901 A1 | 10/2013 | Ochoa | |

FOREIGN PATENT DOCUMENTS

| | | |
|---|---|---|
| AU | 2010286851 A1 | 3/2012 |
| AU | 2010286851 A2 | 5/2012 |
| CA | 2767353 A1 | 1/2011 |
| CA | 2772296 A1 | 3/2011 |
| CN | 1311648 A | 9/2001 |
| CN | 201101603 Y | 8/2008 |
| CN | 102470040 A | 5/2012 |
| DE | 1 197 192 | 7/1965 |
| DE | 8804683 U1 | 6/1988 |
| DE | 202 04 747 | 7/2002 |
| DE | 10329454 A1 | 1/2005 |
| DE | 20 2004 015 328 | 2/2005 |
| DE | 202005007124 U1 | 6/2005 |
| EP | 0657149 A1 | 6/1995 |
| EP | 1159940 A2 | 12/2001 |
| EP | 1588678 A1 | 10/2005 |
| EP | 1743608 A2 | 1/2007 |
| EP | 1985264 A1 | 10/2008 |
| EP | 2200545 A1 | 6/2010 |
| EP | 2451412 A1 | 5/2012 |
| EP | 2473072 A1 | 7/2012 |
| FR | 1 104 562 | 11/1955 |
| FR | 2 757 073 A1 | 6/1998 |
| FR | 2 952 807 | 5/2011 |
| GB | 909 970 | 11/1962 |
| GB | 2133289 A | 7/1984 |
| JP | 2001204851 A | 7/2001 |
| JP | 2004209050 A | 7/2004 |
| JP | 2012011550 A | 1/2012 |
| JP | 2013503268 A | 1/2013 |
| JP | 2013536010 A | 9/2013 |
| WO | 9401496 A1 | 1/1994 |
| WO | 2005086752 A2 | 9/2005 |
| WO | 2005086752 A3 | 9/2005 |
| WO | 2006121413 A1 | 11/2006 |
| WO | 2009017499 A1 | 2/2009 |
| WO | 2009017949 A1 | 2/2009 |
| WO | 2009052031 A1 | 4/2009 |
| WO | 2009068503 A1 | 6/2009 |
| WO | 2011005430 A1 | 1/2011 |
| WO | 2011025675 A1 | 3/2011 |
| WO | 2013016670 A1 | 1/2013 |

OTHER PUBLICATIONS

International Search Report from Corresponding PCT Application No. PCT/US2013/066425 dated Mar. 18, 2014.

Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993, concerning Medical Devices, 2 pages.

Charles T. Mehlman, John P. Schwegmann; Hyphenated History: Knight-Taylor Spinal Orthosis; American Journal of Orthopedics; Jun. 2000; pp. 479-483, vol. 29, Issue 6.

Pamphlet—"Bledsoe Phillippon K.A.F. Positioning Kit", Bledsoe Brace Systems, Medical Technology Inc., 2004, 2 pages.

Posture Control Brace. Soft Form, Orthopaedic by Design, FLA, Orthopedics, Inc., 1 page; 2004. http://www.flaorthopedics.com.

Michael Pfiefer, MD et al., "Effects of a New Spinal Orthosis on Posture, Trunk Strength, and Quality of Life in Wome with Postmenopausal Osteoporosis—a Randomized Trial", American Journal of Physical Medicine & Rehabilitation, vol. 83, No. 3, Mar. 2004, USA, pp. 177-186.

Scoliosis Specialists. About the SpineCor Brace; 2006-2012; http://www.scoliosisspecialists.com/aboutspinecorbrace.html. Retrieved from Internet on Aug. 1, 2013.

Hsu et al., "Principles and Components of Spinal Orthoses", AAOS Atlas of Orthoses and Assistive Devices, 4th Ed., Chapter 7, 2008, pp. 89-111.

Written Opinion of the International Searching Authority Corresponding to International Application No. PCT/US2010/002893.

International Search Report Corresponding to International Application No. PCT/US2010/002893 dated Feb. 22, 2011.

Bledsoe Products, "Philippon K.A.F. Positioning Kit". http://bledsoebrace.com/products/kaf.asp [retrieve from the internet May 10, 2012].

International Search Report from Corresponding PCT Application No. PCT/US20131021170 dated Apr. 12, 2013.

Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.

Supplemental EP Search Report from EP Application No. 98920943, Dec. 7, 2004.

International Search Report from PCT Application No. PCT/US2010/000601, Jun. 28, 2010.

International Preliminary Report on Patentability from PCT Application No. PCT/US2010/000601, Aug. 30, 2011.

International Search Report and Written Opinion of the International Searching Authority Issued in PCT/US2012/043252, Jan. 10, 2013.

Sato, Ena et al., "Effect of the WISH-type hip brace on functional mobility in patients with osteoarthritis of the hip: evaluation using the timed UP & Go", Prosthetics and Orthotics International 2012 36:25 originally published online Nov.17, 201, http://poi.sagepub.com/content/36/125 [retrieved from internet on Jan. 22, 2014].

* cited by examiner

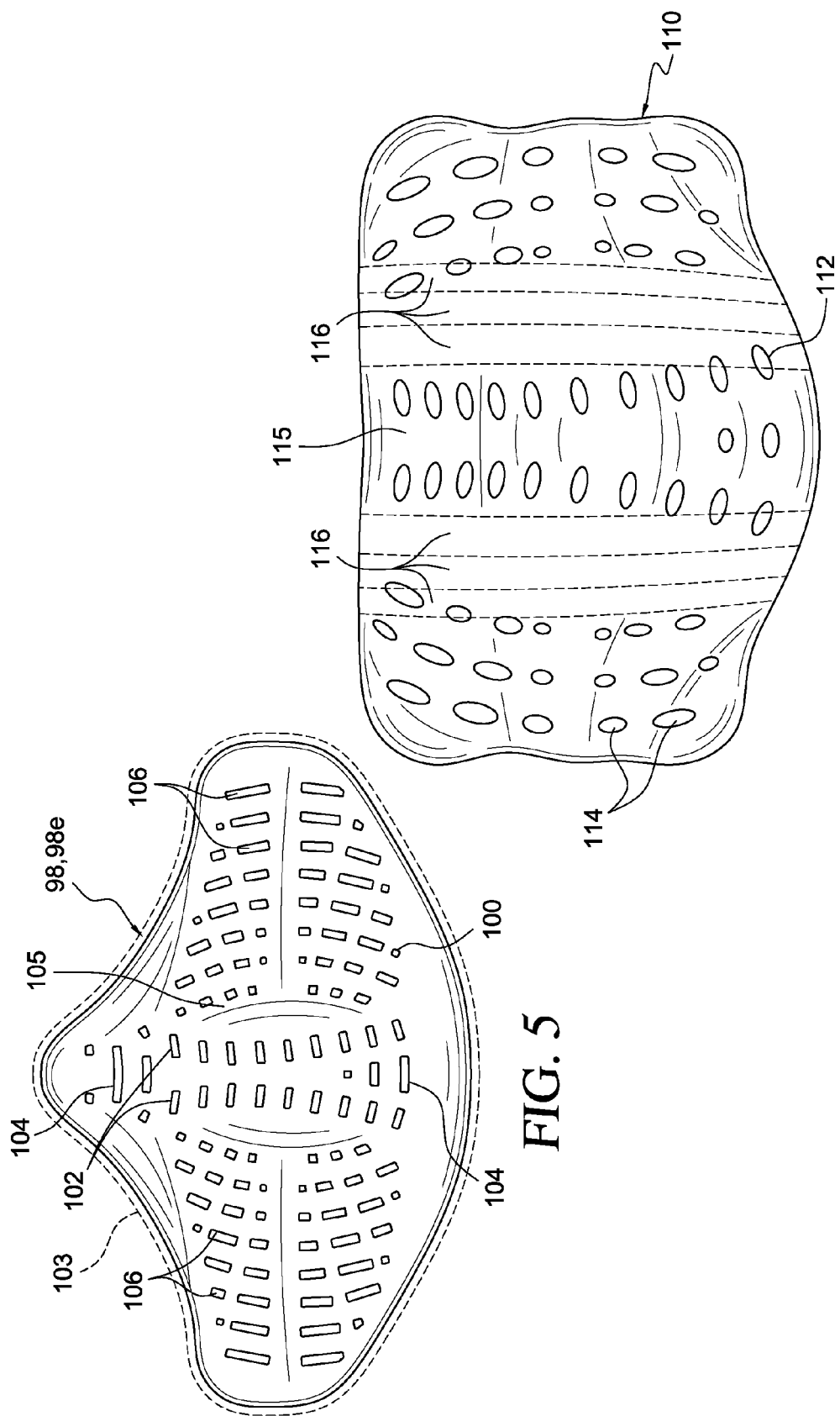

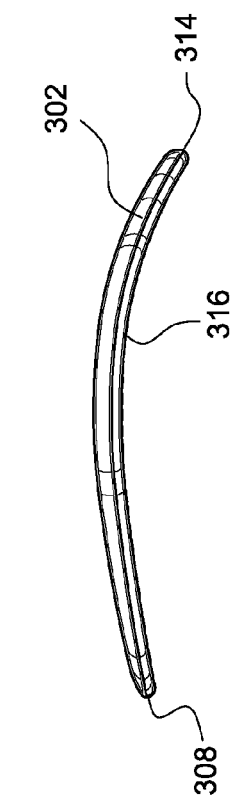
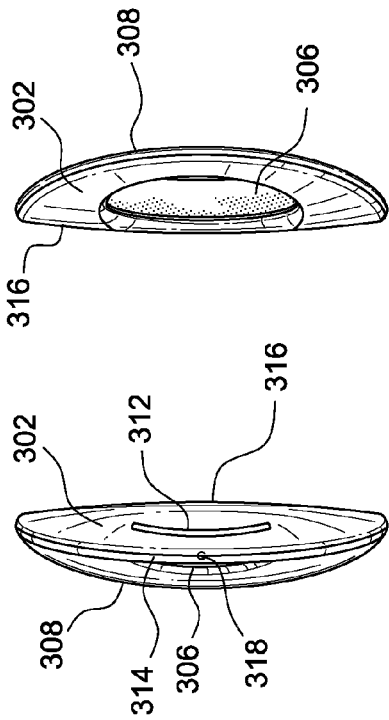
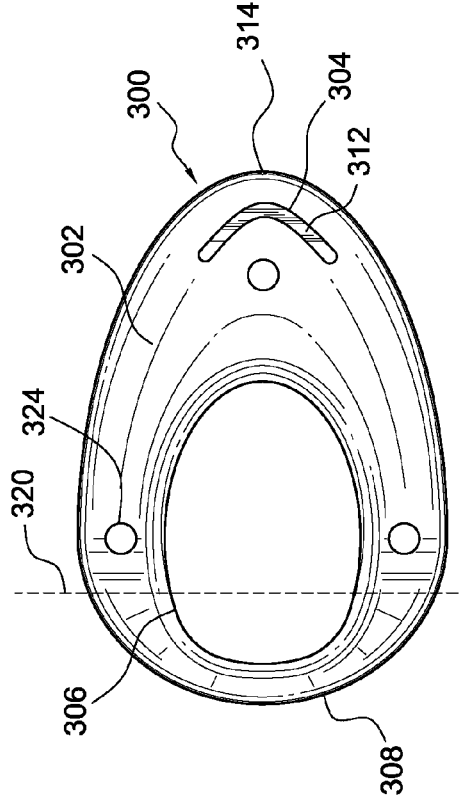
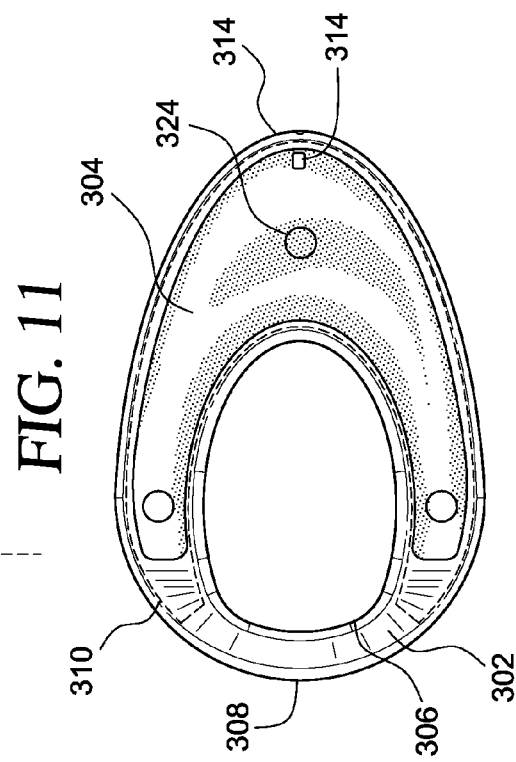
FIG. 13
FIG. 15
FIG. 14
FIG. 11
FIG. 12

ORTHOPEDIC DEVICE FOR TREATMENT OF THE BACK

CROSS-REFERENCE TO RELATED APPLICATIONS

This application is a continuation application of U.S. application Ser. No. 13/249,933, filed Sep. 30, 2011, which is a continuation of U.S. application Ser. No. 12/713,268, filed on Feb. 26, 2010, which claims the benefit of priority from U.S. provisional application No. 61/155,843, filed on Feb. 26, 2009, and U.S. provisional application No. 61/236,649, filed on Aug. 25, 2009. The entirety of each of these provisional applications is incorporated herein by reference.

FIELD OF THE INVENTION

The present invention is directed to an orthopedic device for treatment of the lower back. Embodiments of the device are exemplified for lumbar orthotic management in the particular configuration of a lumbo-sacral orthosis.

BACKGROUND

Many individuals frequently experience chronic lower back pain. Lower back pain is typically managed through rest, analgesics, anti-inflammatory medications, physical therapy, and orthopedic devices or orthoses in the form of lumbar supports. Various types of lumbar supports are available and include sacroiliac (SIO), lumbo-sacral (LSO), and thoracolumbosacral (TLSO) orthoses.

Typical indications for use of lumbar supports include spinal stenosis, herniated discs, post-surgical stabilization, stable and non-displaced spinal fractures, spondylolithesis, spondylolysis, and degenerative spinal pathologies.

One mechanism of action by these lumbar supports includes immobilization of the lower back, by resisting flexion, extension, pelvic tilt, spinal rotation, and lateral bending. Another mechanism is pelvic stabilization in which the lumbar support maintains proper alignment of the pelvis in relation to the spine, and reduces pain in the lumbo-sacral region. Yet another mechanism is hydrostatic lift which occurs when the abdominal cavity is gently compressed, and the intra-abdominal pressure is increased. In yet another mechanism, the lumbar support introduces lordosis support or maintains lumbar support in order to provide correct lumbar lordosis for pain relief, spinal stabilization and improved posture.

Frequently, patients with arthritic hands lack the dexterity to tighten and adjust a lumbar support, as well as in other types of orthopedic devices. Various forms of closure systems, for example hook and loop, buckles, and lacing, have been used to facilitate the closure and retention of these supports on the wearer. However, many of these known forms of closure systems fail to permit adequate easy adjustment of a lumbar support which leads to insufficient exertion of compression on the back of the wearer.

Some closure systems have been proposed which include pulling tensioning elements, for example straps, cables or cords, through a series of guide elements, for example pulleys, posts, rings or eyelets, so as to create a mechanical advantage. Yet many of these known systems suffer from the drawback of friction created on the guide elements when the tensioning elements are adjusted. Another shortcoming is that in many known lumbar supports, a single tensioning element or dual tensioning elements are provided on a single side of the wearer, which in turn leads to rotation of the lumbar support over the wearer's torso when the tensioning element or elements are adjusted. This rotation may lead to the risk of the wearer applying pressure outside the optimal area of the wearer's lumbar region.

Another drawback to known lumbar supports is that because there are so many sizes of the human body, a clinic must maintain many differently sized supports. Even if proper sizes of supports are stocked, a wearer's anatomical shape and size may change over the course of treatment while wearing the device. Some lumbar supports include plates which are universally dimensioned, and are prone to poorly fitting a patient. This leads to inadequate support and discomfort by applying inconsistent or undue pressure over the spinal region and paraspinal musculature of the wearer.

In view of the shortcomings of known lumbar supports, there is a demand for an orthopedic device which is simple to employ but capable of exerting compression against the wearer to effectively treat and stabilize the lower back and other weakened anatomy, is customizable in size, and provides sufficient anatomical support capable of servicing a wide variety of anatomical contours and treatment levels.

SUMMARY

In an embodiment of an orthopedic device of the invention, the orthopedic device is a lumbo-sacral orthosis or lumbar support. The orthopedic device includes a plate, a first elongate belt member having first and second end portions, and a closure system coupling the first belt member to the plate. The closure system is slidably mounted to the plate and arranged to move the first belt member relative to the plate between first and second linear directions. The first belt attachment is secured to the closure system and extends flexibly therefrom. The first belt attachment is removably secured to the second end portion of the first belt member.

In a preferred embodiment, the closure system includes a pulley system and a first elongate tensioning element having a second end connected to the pulley system. The pulley system preferably has a four-to-one ratio, but can also be provided in variations of this preferred ratio. The pulley system includes a first pulley connector including a pin which slidably engages an elongate slot formed by the plate. The first tensioning element is arranged to move the first belt member relative to the plate and a first end of the tensioning element is adjustably securable to the first belt member. The tensioning element may be a cable, cord, strap or other suitable element used to allow the user to apply tension and pressure over the lumbar region of the back via the closure system.

The closure system may include a dosage meter having an indication feature representing tightening settings of the closure system.

In an exemplary embodiment, the orthopedic device also includes a second belt member having first and second end portions. The second end portion of the second belt member connects to the second end portion of the first belt member via the closure system. The closure system includes first and second tensioning elements corresponding to the first and second belt members and the first and second tensioning elements are arranged to extend towards the first end portions of the first and second belt members, respectively. The first end portions of the first and second belt members are arranged to removably secure to one another. In this variation, the closure system comprises a pulley system including first and second pulley connectors mounted on the plate so as to slide in first and second linear directions. The first and second tensioning elements are each secured to the first and second pulley connectors.

The closure system preferably extends over the plate so as to apply pressure onto the plate itself, thereby evenly distributing pressure over the lumbar region of the wearer as the orthopedic device is tightened over a lumbar region of the wearer. The pulley system creates a mechanical advantage, and beneficially employs a four-to-one ratio so as to reduce the travel of the tensioning element. The bearings inside the pulley system reduce friction and facilitate drawing of the tensioning element away from the closure system. Moreover, in the event that two belt members are employed, the orthopedic device uses first and second tensioning elements which correspond to the first and second belt members, and extend in opposed directions. By balancing the load required to tighten the device over the lumbar region, the device eliminates rotation and reduces the load required by each tensioning element. From a combination of these features, the orthopedic device can be effortlessly used to apply intra-abdominal pressure so as to unload and immobilize the spine and provide effective pain relief.

A first handle is secured to the first end of the first tensioning element and is adjustably securable to the first belt member. The first handle has a first end portion and a second end portion which is more rigid than the first end portion. The first tensioning element engages the second end portion of the handle.

In an exemplary embodiment of the handle, the handle has a first handle portion defining a predetermined anatomical shape and formed from at least one resilient material. The handle has a second handle portion more rigid than the first portion. Preferably, the first and second handle portions are integrally secured to one another and are comprised of polymeric materials. The first handle portion is preferably configured to flex over anatomy of a wearer and return to the predetermined anatomical shape when in an unused or unflexed configuration. A hook material may be provided on the handle over an inner surface or a surface facing the belt member. Preferably, a substantial entirety of the outer surface of the first belt member is formed from a hook receivable material so as to allow for the handle to secure over any portion of the first belt member.

Due to the flexibility and resilience of the first handle portion, the handle allows for easy adjustment by the wearer. The handle is anatomically contoured so that is can fully secure to the belt member when worn on wearer, without protruding or causing discomfort to the wearer. The second handle portion is more rigid which makes the handle more durable to withstand the loads when the tensioning element is drawn from the closure system.

In a preferred embodiment, the belt member has a first, predetermined length, and is reducible in length from the second end portion. The first belt member has a plurality of spaced sections arranged for severing with a tool so as to reduce the length of the belt. These spaced sections may be defined from thermoformed regions having thicker and thinner portions, with each thicker portion defining a predetermined sizing dimension and with the thinner portions being preferably the location along which they are severed or cut in order to reduce the length of the belt member.

The first belt member has an outer surface so that regardless of the length of the reduced belt member, the new end portion is arranged to removably engage the first belt attachment. The outer surface may be formed by a loop material capable of securing to a hook material that may be provided on the belt attachment. In order to facilitate the reduction in size of the belt member, the belt member defines a plurality of reduced thickness sections arranged in a predetermined sequence corresponding to different predetermined lengths of the belt member.

A substantial entirety of an outer surface of the first belt member may be formed from a hook receivable material, and a substantial entirety of an inner surface of the first belt member on an opposite side from the inner surface and directed toward a wearer may be formed from a ventilated three-dimensional fabric.

From these features of the belt member, the belt member may be universally sized and therefore accommodate a variety of waist circumferences upon reducing certain lengths of the belt member. Depending on the size of the wearer, a clinician can modify the length of the belt member so as to fit an individual wearer, and over a period of treatment, easily resize the belt according changes in size of the wearer.

The plate may be flexible and anatomically shaped to correspond to a lumbar region of a human back. Specifically, the plate is arranged to relieve pressure over a spinal region of a human back by having an outwardly directed curvature generally protruding away from the spinal region. The plate is also configured to apply even pressure over paraspinal musculature of a human back by having an inwardly directed contour extending over such paraspinal musculature. The plate is configured with the slot to accommodate the closure system so that the slot is at least substantially located over the paraspinal musculature outside of the spinal region of the wearer.

In view of the flexibility and shape of the plate and the location at which the closure system mounts on the plate, pressure is preferably only exerted on the paraspinal musculature thereby providing gentle contact of the orthopedic device over the lumbar region of a wearer. Consequently, pressure spikes are avoided over the lumbar region of the wearer while still providing effective immobilization of the lower back of the wearer.

A rigid panel may be pivotally connected to the plate which allows for hip development, and further aids in automatically adjusting to various anatomies. In the event that the panel is a posterior panel, the posterior panel defines an outwardly directed curvature generally protruding away from the spinal region. The posterior panel applies even pressure over a paraspinal musculature of a human back by having an inwardly directed contour extending over the paraspinal musculature. A rigid panel may also be arranged for an anterior application whereby the panel is adapted to support the abdominal area of a wearer and secure to at least one of the first end portions of the belt members.

The rigid panel may be secured to an inner surface of the orthopedic device, preferably along an inner surface of the plate. In a variation, the plate is covered by a textile cover constructed from a breathable material. The rigid panel is connected to the textile cover at an attachment point so that it pivotally connects to the plate thereby being arranged to accommodate hip movement of the wearer while maintaining support of the lumbar region of the wearer.

Both the plate and the rigid panels may be thermoformable and trimmable to accommodate most body types. They preferably are surrounded with a padding material and define ventilation openings. The plate and rigid panels are shaped to fit the anatomy of wearers, and are anatomically contoured to better immobilize the spine and maximize patient comfort. The particular contours of the plate and the rigid panels prevent pressure on the surgical site and provide pressure on the paraspinal musculature.

BRIEF DESCRIPTION OF THE DRAWINGS

The inventive orthopedic device is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

FIG. 5 is a plan view showing an embodiment of a plate or rigid panel in or for use with the device of FIG. 1.

FIG. 6 is a plan view showing another variation of a plate or rigid panel in or for use with the device of FIG. 1.

FIG. 11 is a top plan view of an embodiment of the handle for use in the orthopedic device of FIG. 9.

FIG. 12 is a rear view of the handle in FIG. 11.

FIG. 13 is a side view of the handle in FIG. 11.

FIG. 14 is a front view of the handle in FIG. 11.

FIG. 15 is a rear view of the handle in FIG. 11.

DETAILED DESCRIPTION OF VARIOUS EMBODIMENTS

A. Overview

Figure 1:
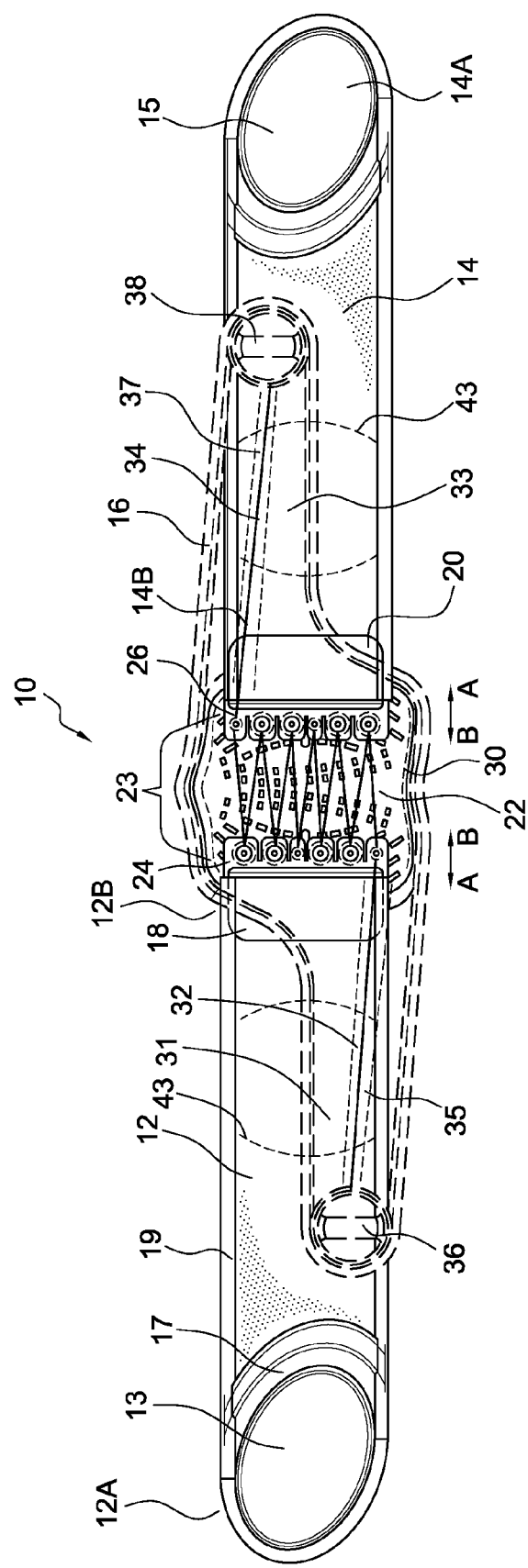
FIG. 1 is a front plan view according to a first embodiment of the orthopedic device according to the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Orthopedic Device and Components for Use Therewith In observing a first embodiment of the orthopedic device shown in FIG. 1, the orthopedic device is in the form of a lumbo-sacral support 10 having first and second elongate belt members 12, 14 each including first and second end portions 12A, 14A; 12B, 14B. The belt members 12, 14 are securable to one another at their first end portions 12A, 14A. The belt members 12, 14 are slidably connected at their second end portions 12B, 14B to a back plate 22, and are coupled to one another via a closure system 23. The closure system 23 is arranged to move the first and second belt members 12, 14 relative to the back plate 22. A cover 16 is secured to the back plate 22 and conceals the closure system 23, and is adjustably securable to the belt members 12, 14.

Figure 2:
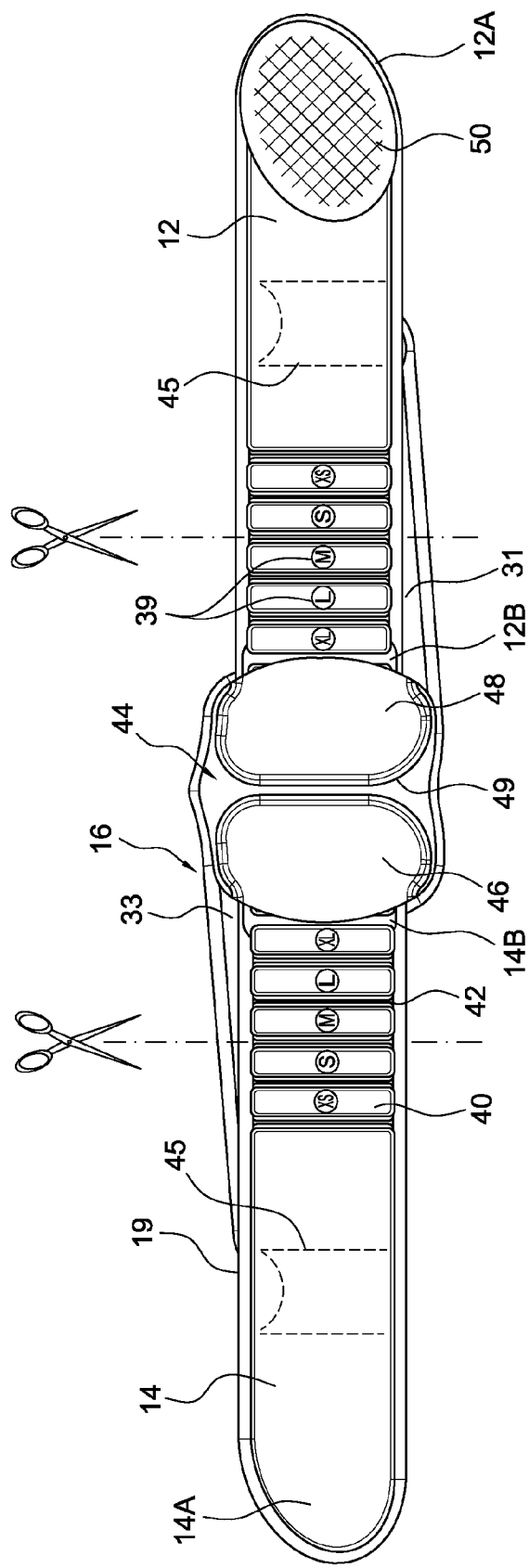
FIG. 2 is a rear plan view showing the embodiment of FIG. 1.

Turning to FIGS. 1 and 2, the belt members 12, 14 each define an attachment portion 13, 15 located at their first end portions 12A, 14A. The front surface of the belt members 12, 14 (as shown in the orientation of FIG. 1) is generally defined as a hook-receiving or loop material. The rear surface of one of the belt members 14 (as shown in the orientation of FIG. 2), has a hook-type material section 50 which is securable over the front surface of either of the belt members 12, 14. This attachment arrangement permits easy adjustment of the belt members about the waist of the wearer.

According to the embodiment shown in FIG. 1, the attachment portions 13, 15 each define corresponding geometric shapes. For example, the illustrated attachment portions have an oval shape which, in combination with properly sizing the belt members for the dimensions of the wearer, allow for easy alignment since the wearer can mate the corresponding shapes to one another. This arrangement allows for the wearer to align the belt members at the same location over repeated uses. Then, upon proper alignment of the belt members, the wearer can just adjust the tension of the support only by pulling the arms and tensioning elements to different locations; the adjustment of the belt members remains constant and it will be easier for the clinician to merely advise just the settings of the arms instead of having to also advise on settings of the belt members relative to one another.

The belt members may be formed from a stretchable or non-stretchable material. Moreover, the belt members may have a padded core with localized areas of increased and decreased padding according to placement locations on the wearer. The belt members may have color coded sections, as in the attachment portions 13, 15, which are provided to direct the wearer as to the particular locations at which the belt members are to secure to one another.

At least in part to minimize uncomfortable pressure exerted on the wearer, the belt members define padded areas 17 surrounding the attachment portions 13, 15. These padded areas may be formed in accordance with thermoforming principles described in U.S. Pat. Nos. 5,334,135, 5,695,452 and 5,823,981, incorporated herein by reference. In addition, the belt members 12, 14 include a padded edging 19 which provides pressure relief along the edges of the belt members against the wearer. Additional padding may be provided anywhere along the device as considered necessary by the wearer or the clinician.

The belt members 12, 14 define an array of thinned sections 42 beginning at the second end portions 12B, 14B and extending toward the first end portion 12A, 14A. Between these thinned sections 42 are padded areas 40 having greater thickness than the thinned sections 42. The thinned sections 42 are preferably trimmable to reduce the length of the belt members 12, 14. A back panel 44 may be secured to a rear side of the back plate 22, and in combination with the padded areas 40, provide compressible padding to the areas surrounding the lumbo-sacral region of the wearer. Alternatively, the back panel may be replaced with a rigid panel of any of the types shown herein, and particularly by example in FIGS. 5-7.

Due to their thinned nature, sections 42 may be provided with some stretchability to the belt members, thereby allowing the belt members to better accommodate the wearer's anatomy and movement. Alternatively, the sections 42 may be formed from stretchable segments connected to the padded areas to greatly enhance any stretching of the belt members. It should be understood, however, that the belt members can be configured to either stretch or not stretch, or have localized areas of increased stretching.

Size selection indicia 39 are provided on the padded areas 40 so as to show particular size configurations. Instead of requiring a vast variety of supports having different lengths, reduced thickness or thinned sections 42 enable easy adjustment in length of the belt members by facilitating reduction of the length of the belt members by cutting along the thinned sections.

For example, the belt members may each have a first predetermined length and are reducible in length from their second end portions. The belt members have a plurality of spaced sections delimited by the thinned sections which allow for severing at these thinned sections in order to reduce the length of the belt. After the belt member has been reduced in length, the new, reduced second end portion of the belt member secures to the closure system.

The belt members may be adaptable to include various drug delivery devices, stiffeners, temperature therapy devices, and electrical stimulation treatment devices. For example, the belt members may be formed using features described in U.S. patent application Ser. No. 11/733,865 and published as U.S. patent application publication 2007/0237808, incorporated herein by reference. Also, the belt members may be configured with attachment or enclosure means or pocket 43 to accommodate other orthopedic devices, such a shell in a hip brace of the type described in U.S. patent application Ser. No. 11/438,474 and published as U.S. patent application publication 2006/0264790, incorporated herein by reference. The belt members also may define closeable pockets 45 to include any of the aforementioned treatment devices.

Figure 3:
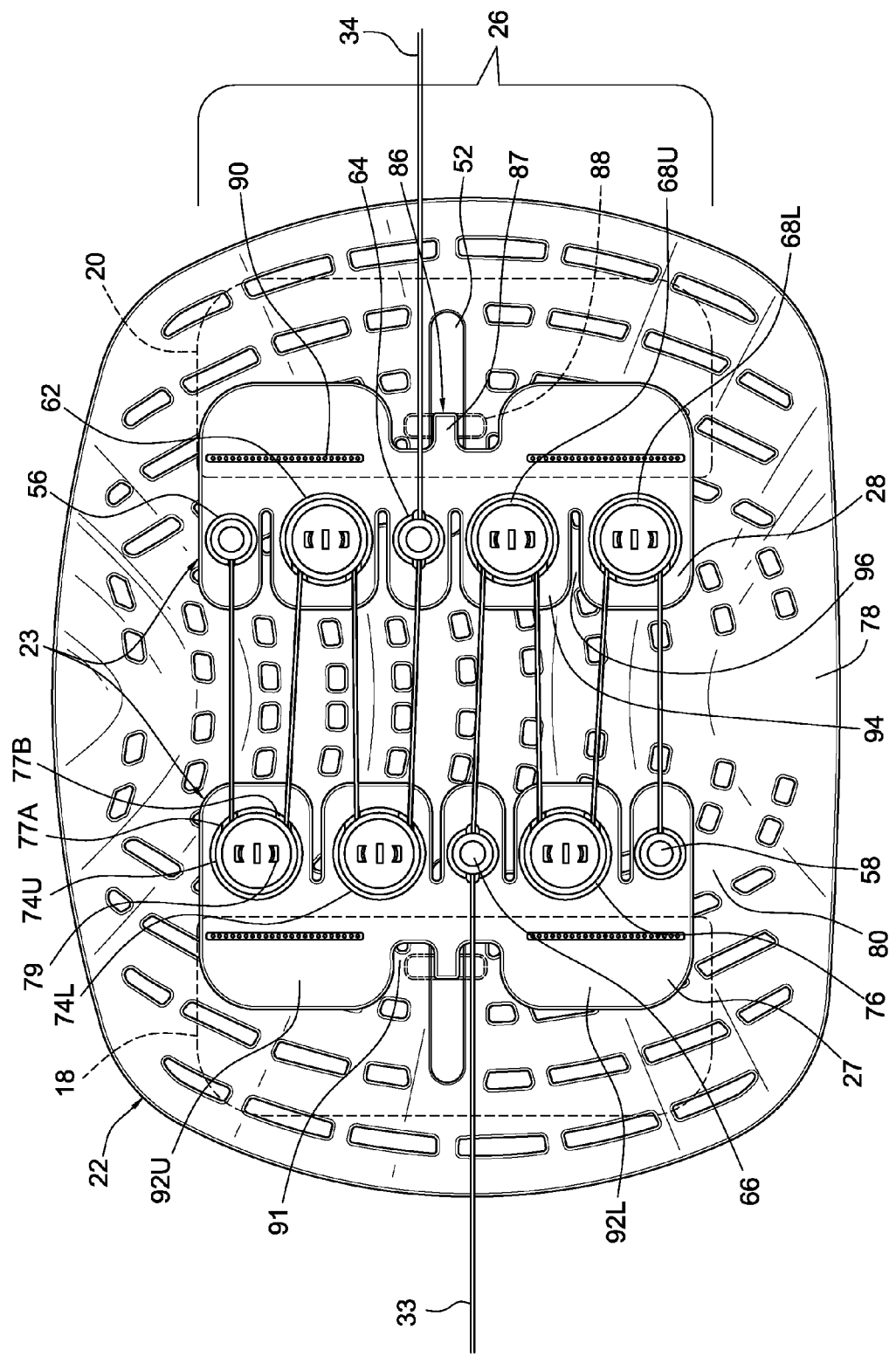
FIG. 3 is a schematic plan view showing an embodiment of a back plate and a variation of the closure system according to the embodiment of FIG. 1.
Figure 4A:
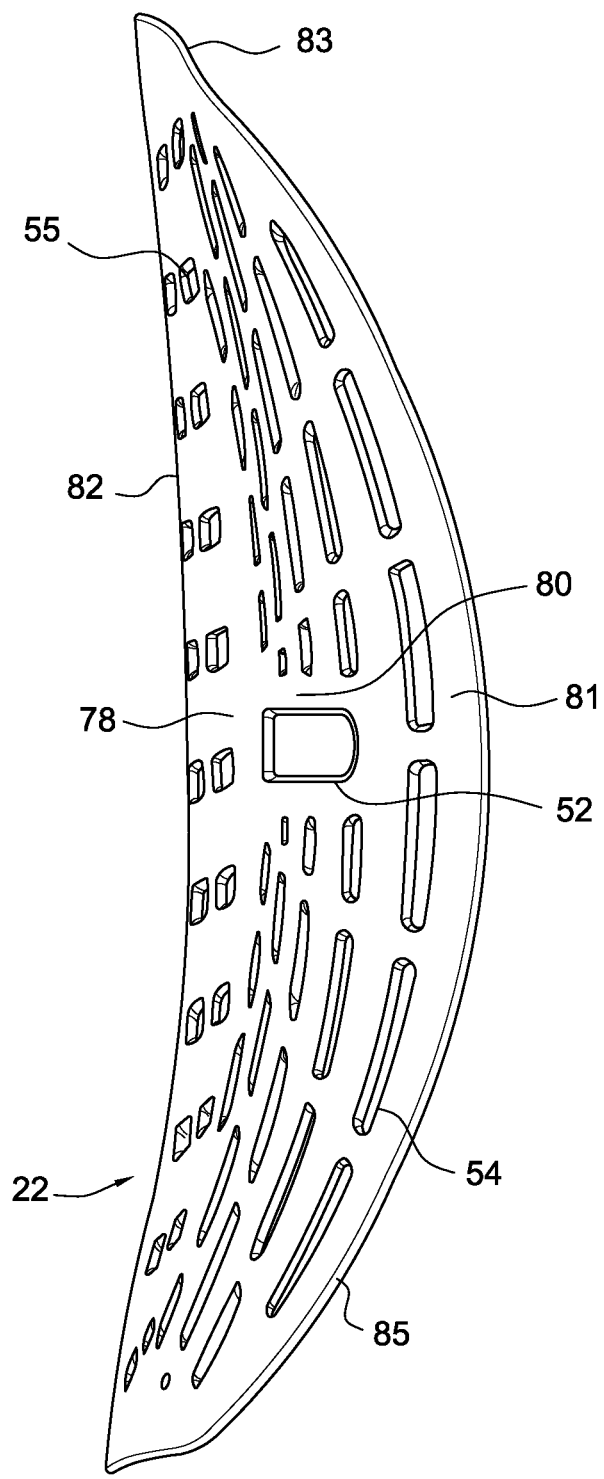
FIG. 4A is a side elevational view showing an embodiment of the back plate.
Figure 4B:
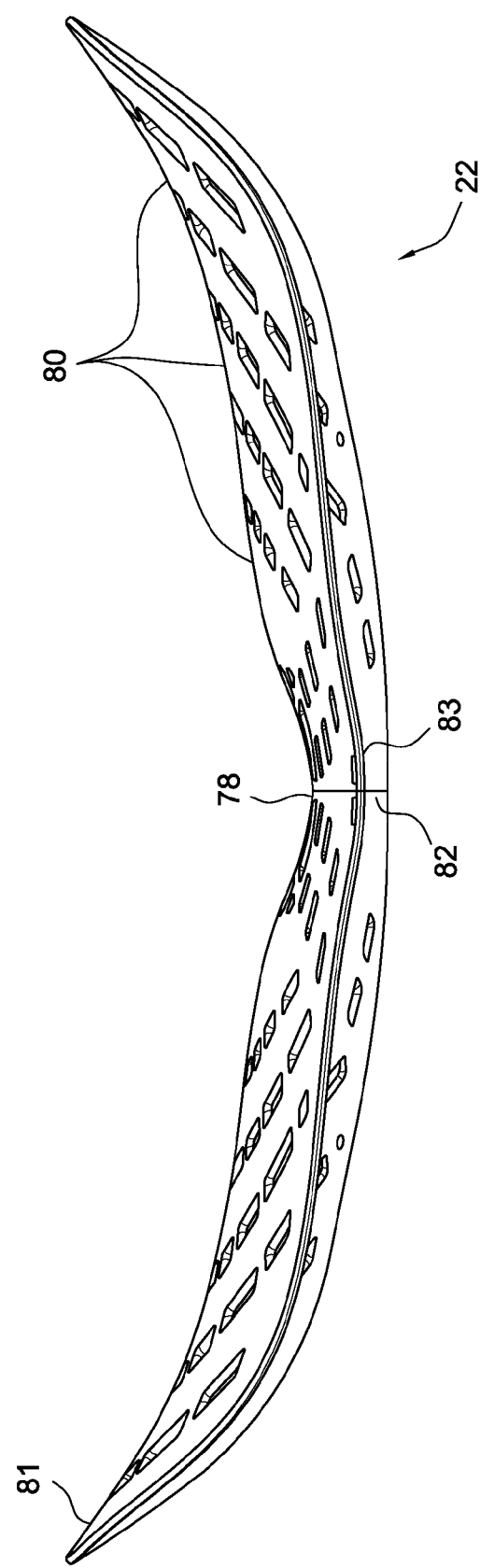
FIG. 4B is a top view showing an embodiment of the back plate of FIG. 4A.

Turning to an embodiment of the back plate in reference to FIGS. 3, 4A and 4B, the back plate 22 slidably connects to the belt members 12, 14. According to this embodiment, the back plate is flexible or bendable to accommodate the anatomy of a wearer's back when the closure system is employed. The ability to bend about the wearer's back is particularly advantageous since the back plate can be used to support a variety of anatomical contours of a single wearer or a variety of wearers. However, while the back plate is bendable about the wearer's back, it provides sufficient rigidity to support the lumbo-sacral region of the wearer. In an alternative, the back plate may be custom formed so as to correspond to exact contours of a particular wearer wherein the back plate is substantially rigid or semi-rigid.

The back plate 22 has a particular anatomical geometry that is arranged to closely accommodate a wide variety of different back anatomies. For example, the plate 22 is configured to relieve pressure over a spinal region of a human back by having an outwardly directed curvature 78 generally protruding away from the spinal region. The plate 22 is arranged to apply even pressure over a paraspinal musculature of a human back by having an inwardly directed contour 80 extending over the paraspinal musculature. The plate 22 includes side wing portions 81 which are inwardly contoured toward the wearer, a tapered top portion 83 and generally rounded side portions 85, which provide coverage over side portions of the lumbar region of a wearer's back, and contribute to better pressure distribution over sensitive and less sensitive areas of a wearer's back.

The plate 22 defines a general arcuate contour 82 which provides lordosis support for the wearer. This contour 82, in combination with pressure exerted on the plate 22 via the closure system, introduces and maintains correct lumbar lordosis for pain relief, spinal stabilization and improved posture. Because the plate is anatomically contoured with the aforementioned features, better hydrostatic lift is also created when the abdominal cavity is gently compressed and the intra-abdominal pressure is increased. Better pelvic stabilization is created by the anatomical shape of the plate since it is arranged to properly align the pelvis in relation to the spine, thereby reducing pain in the lumbo-sacral region of a wearer's back. Again, in combination with closure system, the plate allows for improved immobilization of a wearer's back by immobilizing flexion, extension, pelvic tilt, spinal rotation and lateral bending.

The back plate 22 is formed with a plurality of ventilation openings 54 allowing for a circulation of air between the back of the wearer and back plate 22. The ventilation openings 54 also permit the back plate to be sized larger than conventional back plates since it can cover a greater surface area of the wearer's back without causing undue warming of the wearer's back. Further, since the openings 54 can be arranged in a particular pattern, they can be placed in locations to facilitate greater bending of the back plate, for example at a center pattern 55 extending about the centerline of the back plate and along the outwardly directed curvature 78.

Of particular focus is the back plate variation shown in FIG. 5. Again, as with the back plate 22 of FIGS. 4A and 4B, the back plate 98 has a pattern of openings 100 which are arranged to facilitate both bending along a center line such that a pair of an array of openings 102 is located on opposed sides of the centerline. Also provided between end portions of the pair of an array of openings 102 is another array of openings 106 which further assist in the bending of the back plate 98. On opposed sides of the back plate 98 are patterns of openings which closely follow the contours of the back plate 98 when arranged in a bent configuration. The plate 98 may include an outwardly bowed portion 105 to accommodate the spinal region of a wearer, as well as a plurality of openings 104 extending generally along the spinal region so as to provide enhance breathability and flexibility. A cover 103 of a variety of types may be secured to or surround the plate 98.

Of course, it will be understood that the patterns of the openings defined by the back plate variations shown herein are not limitative, but a variety of patterns fall within the scope of the invention to facilitate bending of the back plate and assist in ventilation the support.

Figure 9:
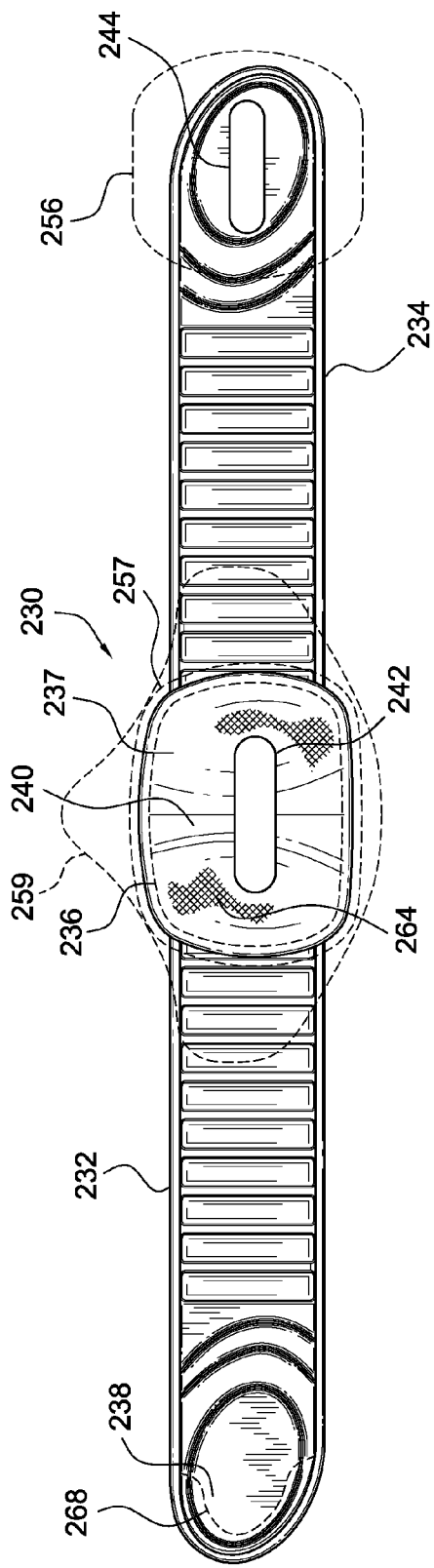
FIG. 9 is a frontal view of another embodiment of the orthopedic device.

The plate shown in FIG. 5 may be arranged as a rigid panel 98R provided in addition to the back plate 22, and may be pivotally connected to an inner side of the plate adjacent a wearer's back, such as at locating element 242 in FIG. 9. The rigid panel may be surrounded by padding material and the padding material may be substantially ventilated using any of the padding materials described herein for use in connection with the belt members and the back plate.

Turning to a variation of the closure system according to the embodiment of FIG. 1, FIG. 3 shows a closure system 23 including first and second pulley systems 24, 26, and first and second tensioning elements 32, 34 coupled to the pulley systems 24, 26 and arranged to tighten the device about the wearer's torso. The pulley systems 24, 26 are connected to the second end portions 12B, 14B of the belt members 12, 14 via belt attachments 18, 20. The closure system 23 is slidably mounted to the plate 22 and arranged to move the belt members 12, 14 relative to the plate 22 between first and second linear directions; outward (A) and inward (B) directions, as shown in FIG. 1.

The tensioning element may be a cable, cord, strap or other suitable element used to allow the user to apply tension and pressure over the lumbar region of the back via the closure system.

The pulley systems 24, 26 include first and second pulley connectors 27, 28 which secure to the first and second belt members 12, 14, respectively, via the belt attachments 18, 20, and secure on opposed sides of the plate 22 in the inwardly directed contour 80 extending over the paraspinal musculature of a wearer's back. The first tensioning element 32 which extends outwardly from the first pulley system 24 at a lower portion whereas the second tensioning element 34 extends outwardly from the second pulley system 26 at an upper portion.

The pulley connector 27 includes a top set of pulleys comprising a top upper pulley 74U and a top lower pulley 74L through which the second tensioning element 34 extends. A first end of the second tensioning element 34 is fixably secured to the anchor post 56 carried by the pulley connector 28. The second tensioning element 34 runs between the top upper pulley 74U on the pulley connector 27 by extending through inlet 77A and outlet 77B and wrapping around a spindle or bearing 79 mounted in each individual pulley. The second tensioning element 34 extends through the top pulley 62 on the pulley connector 28, returning to the top lower pulley 74L, and then being directed through outlet post 64.

The tensioning element 32 is arranged to extend between the pulley connectors 27, 28, while having a first end fixably secured to anchor post 58 carried by the pulley connector 27. The tensioning element 32 also extends between bottom pulleys 68U, 68L located on the pulley connector 28, and the pulley 76 so as to eventually extend through outlet post 66 on the pulley connector 27.

It is preferred, while not limiting, that there are fewer pulleys amounting to an 8:1 pulley system (combined with both pulley connectors, and 4:1 for each tensioning element). It has been found that when there is less travel of the tensioning element through the pulley system, easier adjustment of the pressure on the lumbar region of the wearer is obtained. When combined with the bearings inside the pulleys, there is an elimination of friction which greatly improves the ability for wearers of the device to make adjustments of the tensioning elements. This arrangement leads to improved immobilization of the lumbar region, while providing improved pelvic stabilization, hydrostatic lift and lordosis support.

A sliding arrangement 86 is used to mount the pulley connectors 27, 28 of the pulley systems 24, 26 onto the panel 22. Each pulley connector 27, 28 defines a neck 87 extending outwardly and downward from an outer side (contrasted with an inner side oriented towards the centerline of the back plate). An elongate arm 88 extends in a cross-wise manner from the neck 87.

The neck 87 is arranged to slidably engage a slot 52 formed by the back plate 22, and located in the inwardly directed contour 80 extending over the paraspinal musculature and outside of the outwardly directed curvature 78. The arm 88 retains the neck 87 within the slot 52 and generally slides against a rear surface of the back plate 22 as the second pulley connector 26 is moved relative to the back plate between the directions A, B shown in FIG. 1. The downward bend of the neck 87 may be configured in a manner that permits the second pulley connector to adjustably rotate relative to the back plate in order to permit additional adjustment of the back plate relative to the second belt member.

The pulley connectors 27, 28 each define upper and lower tabs 92U, 92L along the outer side, and a recess 91 in which the sliding arrangement 86 is located. The pulley connectors 27, 28 also define a back mount 74 which are used to retain the belt attachments 18, 20 to the pulley connectors. Because the pulley connectors may be arranged in a resilient or semi-rigid configuration (while permitting some bending to accommodate tightening of the support about the torso of the wearer), a line of apertures 90 are likewise formed by the pulley connectors so as to permit the corresponding belt attachment to be stitched to the pulley connector.

The pulley connectors define a plurality of fingers 94 along the inner side. Each of the fingers 94 carries one of the pulleys, and each finger is spaced by a notch 96. The arrangement of the fingers 94 and the notches 96 permit flexure of the fingers relative to the remainder of the pulley connector, thereby better accommodating the support due to tightening of the tensioning elements.

It is preferable to include opposed tensioning elements of the type shown in the embodiment of FIG. 1 in order to eliminate rotation of the support on the wearer. In effect, the tensioning elements counteract rotation from one another, thereby more securely adjusting to the wearer when the tensioning elements are tensioned.

Accordingly to the embodiment of FIG. 1, the belt attachments 18, 20 are each defined as a pair of flaps having opposed surfaces of hook material. The hook material engages the hook-receiving material of the belt members and effectively couples the closure system to the belt members.

Figure 4C:
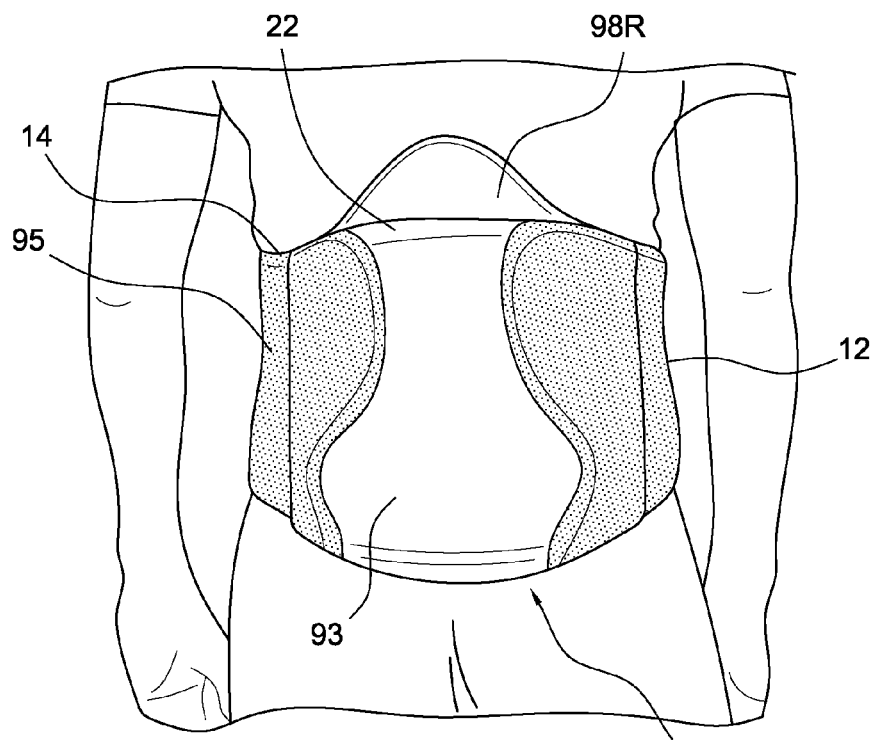
FIG. 4C is a perspective view showing an embodiment of device on a lower back of a wearer which a schematic representation of pressure mapping.

FIG. 4C shows how the advantageous arrangement of the embodiment of the device 230 having a closure system in combination with the plate 22 and associated belt members 12, 14 applies an even distribution of pressure 95 over the paraspinal musculature of a wearer's back. In this instance, a rigid panel 98R is provided in combination with the plate 22, but even without the rigid panel 98R, the even distribution of pressure 95 over the paraspinal musculature may be obtained. As for the spinal region, there is minimal pressure leading to relief 93 exerted on the wearer's back.

Figure 4D:
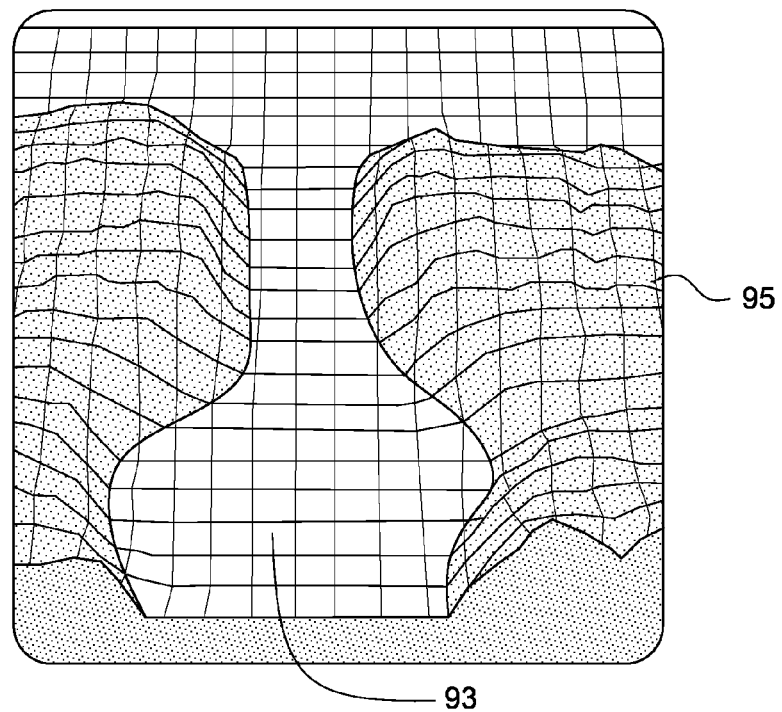
FIG. 4D is a schematic view showing a pressure mapping grid from FIG. 4D.

The result of the combination of these features of the device in FIG. 4C leads to a pressure mapping in FIG. 4D which shows the relief 93 along the spinal region and gentle even contact over the paraspinal musculature in the remaining areas of the lumbar region. It follows that there are no pressure spikes (or at least minimal) which may lead to discomfort when a wearer uses the device.

Referring back to the strap cover, FIG. 1 illustrates that the cover 16 extends over the back plate 22. According to this embodiment, the cover 16 is secured around the back plate 22 with stitching 30 along portions between the belt members 12, 14. The cover 16 defines first and second arms 31, 33 which generally correspond to the first and second belt members 12, 14, respectively. At least the first and second arms 31, 33 are elasticized and are readily positionable relative to the first and second belt members 12, 14.

The first and second arms 31, 33 define first and second channels 35, 37, respectively, through which the first and second tensioning elements 32, 34 extend, respectively. The channels 35, 37 may be formed in a variety of constructions, but it is preferable that they conceal the tensioning elements so as to prevent the tensioning elements from catching on any object that the wearer may contact or any clothing. For example, in embodiment of FIG. 1, the channels are sewn into two layers of material used to form the arms 31, 33. Alternatively, channels may be formed along the surface of the cover by adding a strip layer of material.

Each of the arms 31, 33 includes a handle 36, 38 which is secured to an end portion thereof. A second end of each tensioning element is secured to the handle 36, 38. The handle 36, 38 may be formed in a variety of different configurations, for example as having a raised handle portion of the type shown in FIG. 1 which permits the wearer to insert fingers into the handle portion to better grasp the handle and thereby easily tighten the arms (and tensioning elements) relative to the belt members. Of course, other grasping configurations are possible which allow for the wearer to easily grasp the end portions of the arms, as will be shown in FIGS. 11-15.

Each end portion of the arms includes an attachment portion which allows for securing the arm end portions relative to the belt member. For example, the outer surface of the belt members may be formed from a hook-receiving material and an inner side of the arms at a location generally corresponding to the handle may include a hook patch. Therefore, upon drawing the arms away from the back panel and by the tensioning elements, the wearer can secure the handles at a variety of locations on the belt members to tighten the support about the torso of the wearer.

In a variation of the cover, the handles may be removable from the arms and the tensioning elements so that the arms can be folded over to reduce their length for certain wearer's of the support having a narrower torso. Once the arms are properly sized, the handle may be attached to the arm having a reduced length and the tensioning element can accordingly be reattached.

In observing FIG. 2, the back panel 44 has cushioning features that are arranged to be adjacently placed against the wearer to provide comfort to the wearer. In particular, as the arms are tightened relative to the belt members, the pressure exerted against the wearer is minimized by the back panel. The back panel comprises first and second padded regions 46, 48 which are spaced by a thinned transition area 49. The transition area 49 permits better bending of the back panel 44 as the back plate 22 is similarly bent to accommodate the wearer.

The back panel 44 is shaped in an ergonomic form much like the aforementioned form of the back plate 22. Further, the back panel 44 may be formed from a ventilated three-dimensional fabric or a thermoformed padding material or combination thereof, as discussed above in connection with the belt members, so as to work in combination with the ventilation openings of the back plate to better provide a circulation of air through the support to allow for added comfort to the wearer.

FIG. 6 illustrates an embodiment of a front plate 110 which may be used in combination with the support 10. The front plate 110 removably secures to the inner surface of the belt members. The front plate 110 defines a pattern of openings 112, in a similar manner to the openings 102 of the back plate 98, which assist in bending the front plate about the torso when tightened against the user. The front plate 110 also defines a plurality of ventilation openings 114 which further assist in permitting a circulation of air to make the support more comfortable to the wearer. A plurality of openings 115 are particularly provided along the spinal region to provide ventilation and flexibility.

The front plate may be wrapped with a fabric material, such as a three-dimensional fabric of any type described by U.S. patent application Ser. No. 11/723,604 and published as U.S. patent application publication 2007/0185425, incorporated herein by reference. The fabric may be combined with a padding material, such as foam, and is preferably breathable so as to work in combination with the ventilation openings.

As depicted by the sections 116 in FIG. 6, the front and back plates may define a surface curvature (resulting in the plates having a curved cross-section) which follows the contours of general human anatomy. In other words, the front and back plates are not flat plates, but have a specific geometry which applies more even pressure onto the wearer than in conventional flat plates. For example, surface curvatures in the back plate can lift the plate away from the spinal column of the wearer and apply even pressure on either side of the spinal column so as to form a shape which imparts a very rigid plate when placed proximate to the wearer with a thin sheet of plastic forming the plate. It will be understood, however, that the support is not limited to including curved front and back plates; conventional flat plates may be employed.

Figure 7:
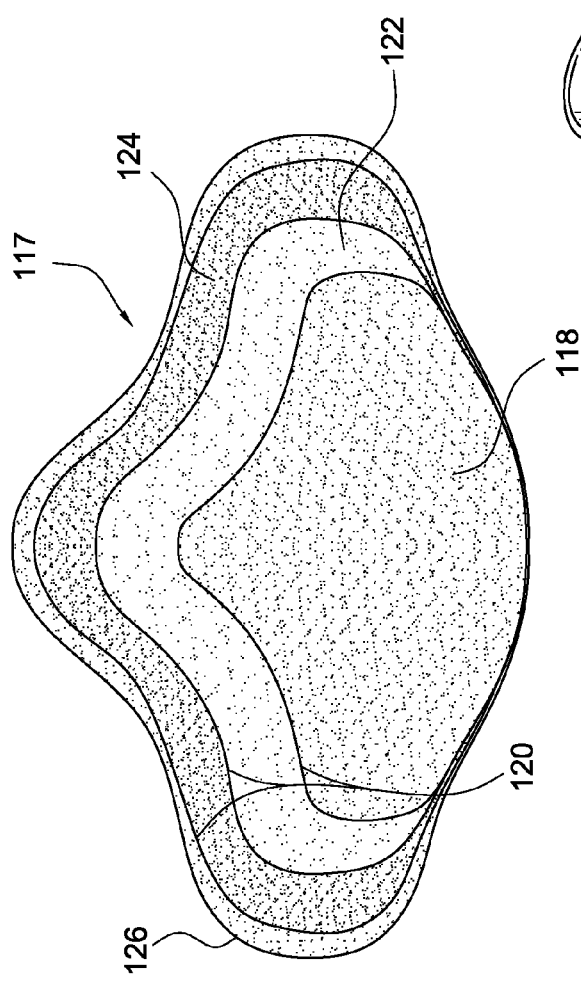
FIG. 7 is a plan view showing another variation of a plate or rigid panel in or for use with the device of FIG. 1.

As illustrated in FIG. 7, a variation of the back plate or rigid panel 117 is shown having a variety of different size configurations 118, 122, 124, 126. These size configurations each have a trim line 120 which is formed by a reduced thickness enabling the clinician to trim the back plate to a suitable size corresponding to the wearer. The back panel and the front plate may also have such trim lines so that the entirety of the support along with the belt members may be modified to the appropriate size of the wearer.

Figure 8:
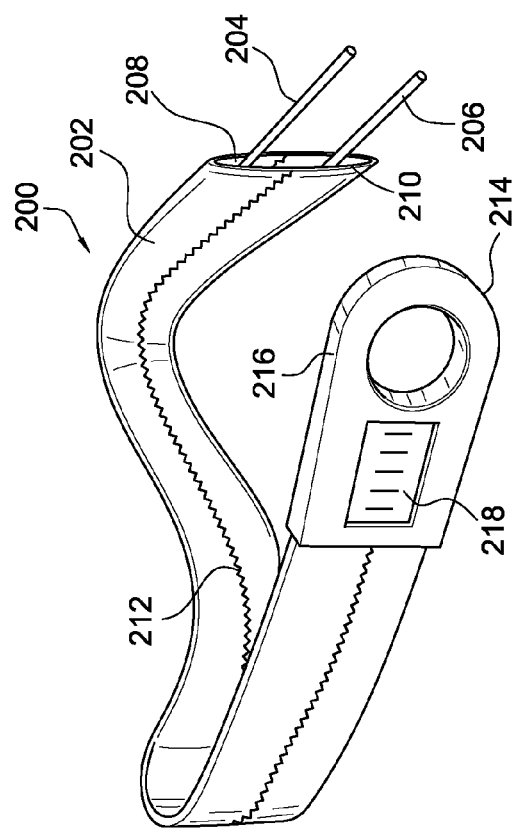
FIG. 8 is a perspective schematic view of another embodiment of a strap cover of the orthopedic device.

In referring to FIG. 8, an embodiment of the arms belonging to the cover is shown as having a dosage meter. In this variation, the arms comprise a strap 200 having a strap body 202 divided by a stitched divider 212. The divider 212 forms upper and lower channels 208, 210 through which upper and lower tensioning elements 204, 206 connecting to a closure system are inserted. The tensioning elements 204, 206 secure to a handle 214 having a grasping feature 216 in the form of an opening.

The tensioning elements 204, 206 are connected to a tension meter 218 which provides indicia showing relative degrees of tightening of the tensioning elements about the torso of the wearer. The tension meter may include a spring which elongates at prescribed tension settings which can correspond to indicia. The purpose of the tension meter is to provide a calibrated load that is measured by the clinician so that instructions can be given to the wearer at which tension setting the wearer should adjust the tensioning elements.

In a variation, the tension meter may include printing on an elastic segment which is revealed once the tensioning elements and the elastic are stretched to a certain point.

Figure 10:
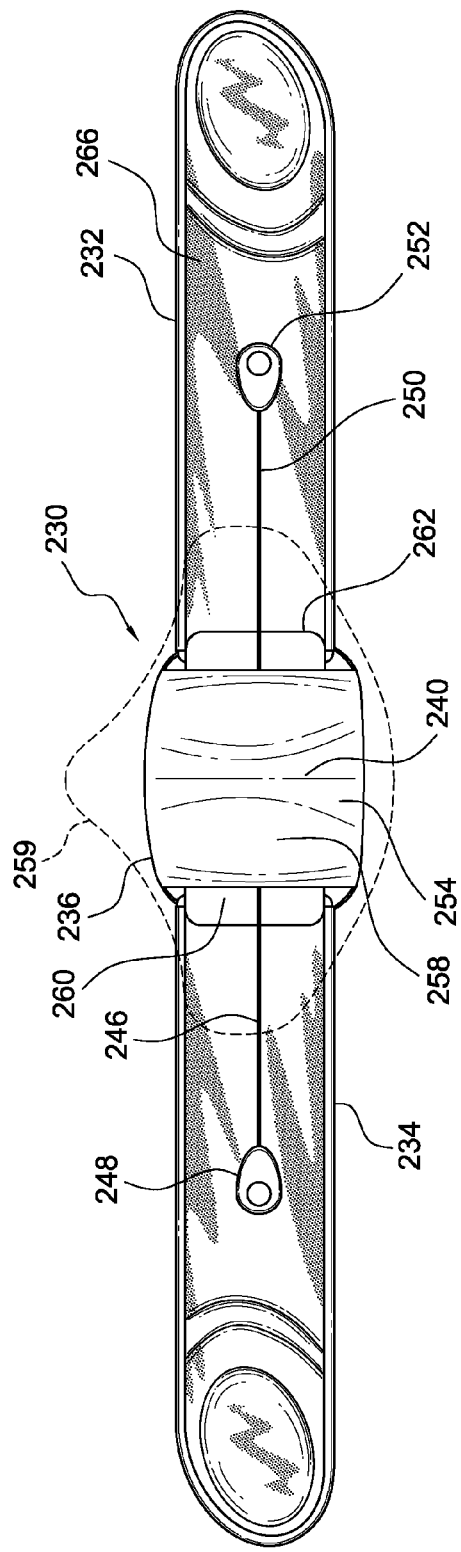
FIG. 10 is a rear view of the orthopedic device of FIG. 1.

In observing FIGS. 9 and 10, another embodiment of the orthopedic device is shown bearing some features different from the embodiment of FIG. 1. According to this embodiment, the device 230 includes first and second belt members 232, 234 which are secured to a back plate 236 via belt attachments 260, 262. The back plate 236 is shown as having a covering 237. The back plate 236 is contoured down the middle or spinal region 240 to correspond to the anatomy of the lower back or lumbar region of the back, as well as regions 254, 258 outside the middle region 240 in a manner described above in connection with other embodiments of the back plate. A breathable covering 264 surrounds portions of the periphery of the back plate 236.

The first belt member 232 includes a fastening element 238 located on the inner surface, such as hook material, which secures to the outer surface of the second belt member 234.

An inner surface of the covering 237 includes a locating element 242 which allows for the user to align and mate to a corresponding supplementary support element thereto. For example, a bladder system 257, which is either inflatable or pre-inflated, may be secured to the covering 237. By providing the locating element, the wearer can be assured that the supplementary support element is positioned in the proper location. Alternatively, a rigid panel 259, such as the rigid panel 98R may be secured at the locating element 242 so as to provide additional support to the plate.

The locating element 242 may be a colored patch having a contrast relative to the color of the covering which is adapted to engage hook elements located on a supplementary support element. The end portion of the second belt member 204 may likewise include another locating element 244 which is located on the front of the user or abdominal region, and arranged to receive another supplementary support element, such as an anatomically contoured front plate 256.

As shown in FIG. 10, the device 230 includes a closure system which uses tensioning elements 246, 250 having handles 248, 252 located at the end thereof. The tensioning elements 246, 250 are exposed and the handles 248, 252 are adapted to engage a hook receivable outer covering 266 of the belt members 232, 234. A hook element 268 is provided on the belt member 232 to secure to the outer covering.

Turning to FIGS. 11-15, an example of a handle 300 useable in the device 230 shown in FIGS. 9 and 10 is depicted.

FIG. 11 illustrates the handle 300 as including a first part 302 which definitively defines a periphery of the handle 300. A second part 304 is integrally secured to the first part 302, and is at least exposed on the inner surface of the handle 300, as shown in FIG. 12. The second part 304 extends from the mid-span 320 to the front portion 314 of the handle 300. The first part 302 is substantially flexible, and the second part 304 is more rigid than the first portion 302.

In accordance with one variation, the first part 302 is constructed from a polymeric material having flexibility and resiliency. The second part 304 is also constructed from a polymeric material which is substantially rigid. The first and second parts are integrally secured to one another forming a single component. A leading section 312 of the second part 304 is exposed on the outer surface at the front portion 314, as depicted by FIG. 11, whereas the entirety of the periphery of the second part 304 is exposed on the inner surface of the handle, as depicted by FIG. 12. As shown in FIGS. 13-15, the second part 304 is retained within the first part 302, and is flush with the periphery of the first part 302.

The handle 300 defines an opening 306 located near a mid-span 320 and rear portion 308 of the handle 300. The rear portion 308 of the handle, as delimited by one end of the mid-span at 320, is substantially flexible due to the lack of the second portion 304. On an undersurface of the handle, as depicted in FIG. 12, a patch of hook material 310 extends from the front portion 314 to an end of the mid-span delimited by line 320, and the hook material 310 tracks at least the periphery of the second part 304. This allows for the user to easily flex and remove the handle 300 from the outer surface of the belt members. In other words, in an inner surface of the handle may include a hook material located at the second handle portion and only at a location on the first handle portion adjacent the second end portion In yet another variation, anchors having a shape generally conforming to at least part of the handles may be secured to the belt members so that the handle is secured at the anchors. The anchors can have a retention wall which includes a lip preventing further movement of the handle relative to the back plate so as to define a maximum tension that the wearer should set the arms. The clinician can set the anchors at various locations on the belt members as the treatment of the wearer changes, and more or less tension is required.

The handle 300 includes a recess 316 for securing to the cord belonging to the closure system. An opening 318 at the middle of the thickness of the handle is defined which is in communication with the recess 316. The opening 318 is located at the front portion 314 through which the cord extends to the closure system thereby assuring that the cord is pulled generally along the axis of the handle.

As illustrated in FIG. 13, because the second part 304 is substantially rigid, the handle 300 is contoured with bend 316 so as to be anatomically compliant to the torso of the wearer.

Suitable fasteners 324, such as rivets, may be used to secure the hook material onto the handle 300. In variations, other types of fasteners may be used in place of hook and loop material to secure the tensioning elements to the handles. Examples include buckles, snaps and other suitable types of corresponding fasteners on the belt members and the handles.

While the foregoing embodiments have been described and shown, it is understood that alternatives and modifications of these embodiments, such as those suggested by others, may be made to fall within the scope of the invention. Moreover, any of the principles described herein may be extended to any other orthopedic devices.

The invention claimed is:

1. An orthopedic device comprising:
an elongate belt member having first and second ends;
a plate slidably connecting to the belt member, the plate being bendable to accommodate anatomy of a wearer and rigidly supporting anatomy of the wearer as the belt member is tensioned;
a closure system located on a posterior side of the orthopedic device and arranged for placement for a back of the wearer, and at least one elongate tensioning element arranged to tighten the device about a user, the at least one tensioning element having a first end connecting to the closure system and a second end releasably securing to the belt member, the closure system connecting the first end of the belt member to the plate, the closure system freely movably connecting to the plate within a predetermined range in response to movement of the at least one tensioning element relative to the second end of the second end of the belt member;
wherein the plate includes side wing portions inwardly contoured toward a wearer, a tapered top portion and generally rounded side portions.

2. The orthopedic device according to claim 1, wherein the plate is arranged for securing against a lumbo-sacral region of a wearer, and is configured to relieve pressure over a spinal region of a human back by having an outwardly directed curvature generally arranged to protrude away from a spinal region of a wearer.

3. The orthopedic device according to claim 1, wherein the plate is arranged for securing against a lumbo-sacral region of a wearer, the plate being arranged to apply even pressure over paraspinal musculature of a human back by having an inwardly directed contour arranged to extend over paraspinal musculature.

4. The orthopedic device according to claim 1, wherein the closure system extends at least in part over the plate and is arranged to exert pressure over the plate onto the anatomy of the wearer, the plate defining a generally arcuate contour.

5. The orthopedic device according to claim 1, wherein the plate defines a plurality of ventilation openings.

6. The orthopedic device according to claim 5, wherein the plurality of ventilation openings are arranged in a pattern to facilitate bending along a vertical center line defined along the plate.

7. The orthopedic device according to claim 6, wherein the plurality of ventilation openings are defined along opposed sides of the centerline.

8. The orthopedic device according to claim 1, wherein the plate defines an outwardly bowed portion arranged to accommodate a spinal region of a wearer, and a plurality of openings extending generally along the spinal region.

9. An orthopedic device comprising:
an elongate belt member;
a plate slidably connecting to the belt member, the plate being bendable to accommodate anatomy of a wearer and rigidly supporting anatomy of the wearer as the belt member is tensioned;
a closure system connecting the belt member to the plate, the closure system movably connecting to the plate within a predetermined range;
a rigid panel pivotally connected to an inner side of the plate adjacent to anatomy of a wearer.

10. The orthopedic device according to claim 9, further comprising padding material surrounding the rigid panel.

11. The orthopedic device according to claim 9, wherein the rigid panel defines a plurality of trim lines representing differently sized profiles.

12. The orthopedic device according to claim 9, wherein the closure system is slidably mounted to the plate and arranged to move relative to the plate between first and second directions when worn by a user.

13. The orthopedic device according to claim 9, further comprising a substantially rigid anterior panel arranged for connecting to the belt member against a wearer's abdominal region, wherein the plate is arranged as a posterior plate adapted to secure against a wearer's back at the lumbo-sacral region.

14. An orthopedic device comprising:
an elongate belt member;
a plate slidably connecting to the belt member, the plate being bendable to accommodate anatomy of a wearer and rigidly supporting anatomy of the wearer as the belt member is tensioned;
a closure system connecting the belt member to the plate, the closure system movably connecting to the plate within a predetermined range;
a substantially rigid anterior panel arranged for connecting to the belt member against a wearer's abdominal region, the plate being arranged as a posterior plate adapted to secure against a wearer's back at the lumbo-sacral region.

15. The orthopedic device according to claim 14, further comprising padding material surrounding the rigid anterior panel.

16. The orthopedic device according to claim 14, wherein the rigid anterior panel defines a plurality of trim lines representing differently sized profiles.

* * * * *